United States Patent [19]

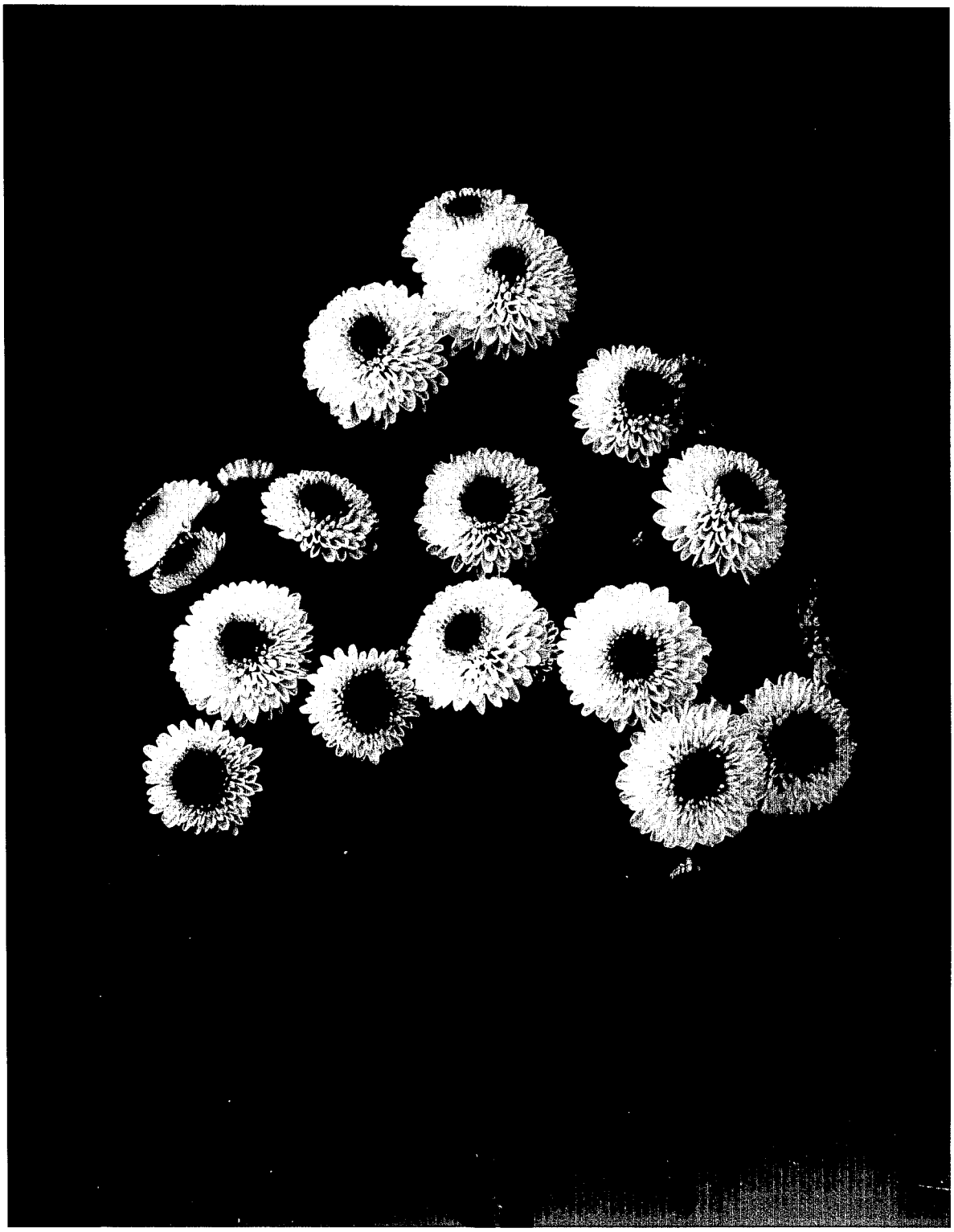

Van Der Knaap

[11] Patent Number: Plant 6,735

[45] Date of Patent: Apr. 11, 1989

[54] CHRYSANTHEMUM PLANT NAMED GREEN PEAS

[75] Inventor: Jacques C. M. Van Der Knaap, De Lier, Netherlands

[73] Assignee: Fides Beheer B.V., De Lier, Netherlands

[21] Appl. No.: 123,902

[22] Filed: Nov. 23, 1987

[51] Int. Cl.[4] ..... A01H 5/00

[52] U.S. Cl. ..... Plt./77

[58] Field of Search ..... Plt./74–82

*Primary Examiner*—James R. Feyrer

*Attorney, Agent, or Firm*—Foley & Lardner, Schwartz, Jeffery, Schwaab, Mack, Blumenthal & Evans

[57] ABSTRACT

A Chrysanthemum cultivar named Green Peas, having a white mature ray floret color which becomes yellow toward the center of the flower which is a medium green. The cultivar is a pompon type with a diameter across the face of the capitulum of 40–50 mm. The overall effect of the white to yellow to green color in the center presents a very striking appearance.

1 Drawing Sheet

The present invention comprises a new and distinct cultivar of *Chrysanthemum morifolium,* hereinafter referred to by the cultivar name Green Peas.

Green Peas is a product of a planned breeding program which had the objective of creating new Chrysanthemum cultivars with pompon capitulum type, white-green ray florets, 8 weeks response, and the ability to produce commercially acceptable quality in year-round cut mum programs. Such traits in combination were not present or needed improvement in previously available commercial cultivars.

Green Peas was originated from a hybridization made by applicant in a controlled breeding program in De Lier, Holland in 1984. The female parent was Ping Pong, an unpatented variety which was commercialized briefly in Holland. The male parent of Green Peas was a first generation hybrid having the parents Pink Pompon and Orca.

Green Peas was discovered and selected as one flowering plant within the progeny of the stated parentage by Jacques C. M. Van der Knaap in August 1984 in a controlled environment in De Lier, Holland.

The first act of asexual reproduction of Green Peas was accomplished when vegetative cuttings were taken from the initial selection in October 1984 in a controlled environment in De Lier, Holland by a technician working under formulations established and supervised by Jacques C. M. Van der Knaap. Horticultural examination of selected units initiated in April 1985 has demonstrated that the combination of characteristics as herein disclosed for Green Peas are firmly fixed and are retained through successive generations of asexual reproduction.

Green Peas has not been observed under all possible environmental conditions. The phenotype may vary significantly with variations in environment such as temperature, light intensity, and day length. The following observations, measurements and comparisons describe plants grown in De Lier, Holland under greenhouse conditions which approximate those generally used in commercial practice.

The following traits have been repeatedly observed and are determined to be basic characteristics of Green peas, which in combination distinguish this Chrysanthemum as a new and distinct cultivar:

1. Pompon type.

2. Green to white ray florets. When opening, the green is dominant, but as the flower fully opens and matures, the ray florets become white. The overall effect is very striking.

3. Diameter across the face of the capitulum is 40–50 mm.

4. Green (immature) to green and yellow (mature) disc florets.

Of the many commercial cultivars known to the present inventor, the most similar in comparison to Green Peas is Ping Pong. In comparison to Ping Pong, Green Peas has bigger leaves, and green ray florets in the center and cream white ray flowers in the other rows of petals. The capitulum form and capitulum type are similar to those same characteristics of Ping Pong.

The accompanying photographic drawing shows in perspective view typical inflorescence and foliage characteristics of Green Peas, with colors being as nearly true as possible with illustrations of this type.

In the following description, color references are made to the Royal Horticultural Society Colour Chart. The color values were determined between 11:00–12:00 a.m. in September, 1985 under natural daylight at De Lier, Holland.

Classification:

*Botanical.*—*Chrysanthemum morifolium,* Ramat., cv. Green peas.

*Commercial.*—Cut, decorative spray.

INFLORESCENCE

A. Capitulum:

*Form.*—Flat.

*Type.*—Decorative.

*Diameter across face.*—40–50 mm.

B. Corolla of ray florets:

*Color (general tonality from a distance of three meters).*—Green and white.

*Color (upper surface).*—155B when mature, becoming yellow-white 145B near center.

C. Corolla of disc florets:

*Color (mature).*—Yellow, approximately 8A-B.

*Color (immature).*—Green, approximately 145B, darker at center.

D. Reproductive organs:

*Androecium.*—Present only in disc florets, few.

*Gynoecium.*—Present in both disc and ray florets, numerous.

PLANT

A. General appearance:
*Height.*—85 cm.
B. Foliage:
*Color* (*upper surface*).—146A.

*Color* (*under surface*).—148B.
*Shape.*—Pinnately lobed.

I claim:

1. A new and distinct cultivar of Chrysanthemum named Green Peas, as illustrated and described, and parts thereof.

* * * * *